United States Patent [19]

Warriner

[11] Plant 4,767

[45] Sep. 22, 1981

[54] ROSE PLANT—73-3521

[75] Inventor: William A. Warriner, Tustin, Calif.

[73] Assignee: Jackson & Perkins Co., Medford, Oreg.

[21] Appl. No.: 131,393

[22] Filed: Mar. 18, 1980

[51] Int. Cl.[3] ..... A01H 5/00

[52] U.S. Cl. ..... Plt./20

[58] Field of Search ..... Plt./20

*Primary Examiner*—Robert E. Bagwill

*Attorney, Agent, or Firm*—Klarquist, Sparkman, Campbell, Leigh, Whinston & Dellett

[57] ABSTRACT

A vigorous rose plant of upright habit reaching over seven feet in height. Possesses long, stiff stems with fewer thorns than parent Tonight. Leaves are dark green of medium size. Flower is of uniform red color with light fragrance.

1 Drawing Figure

The present invention relates to a new and distinct cultivar of rose plant of the hybrid tea class which was originated by me by crossing an unnamed variety with pollen of the variety, Tonight, U.S. Plant Pat. No. 3,522.

This objective was substantially achieved along with other desirable improvements as evidenced by the following unique combination of characteristics which are outstanding in this new cultivar and which distinguish it from its parents as well as from all other cultivars of which I am aware:

1. A very vigorous plant reaching over seven feet in height.
2. Long, stiff stems with fewer thorns than its parent, Tonight.
3. Leaves of dark green, medium size, smaller than those of rose Forever Young, U.S. Plant Pat. No. 2,443 (a grandparent variety).
4. A uniform red flower color of near RHS 44A with very little change from fresh bud to falling petals.
5. A pleasant although light fragrance.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of color is indicated.

Parentage:
- *Seed parent.*—Unnamed variety.
- *Pollen parent.*—Tonight.

Classification:
- *Botanical.*—Rosa hybrid.
- *Commercial.*—Hybrid tea.

FLOWER

Observations made from specimens grown at Irvine, Calif., in September of 1979.

Blooming habit: Continuous.

Bud:
- *Size.*—1½" when petals start to unfurl.
- *Form.*—Pointed ovoid.
- *Color.*—When sepals first divide near 53A; when half blown; upper side of petals near 44A, lower side of petals near 46C.
- *Sepals.*—Color: outer surface 138B; three appendaged sepals lightly appendaged; two unappendaged sepals hairy edged.
- *Receptacle.*—Color: 138B. Shape: narrow funnel. Size: long. Surface: smooth.
- *Peduncle.*—Length: long. Surface: prickly. Color: light green. Strength: stiff, erect, heavy.
- *Opening.*—Outer petals curl slightly, leaving the center pointed, inner petals tips only recurve.

Bloom:
- *Size.*—Large. Average open size 4"–5".
- *Borne.*—Singly.
- *Stems.*—Very long, strong.
- *Form.*—When first open, high centered. Permanence: retains its form to the end; outer petal edges slightly curled.
- *Petalage.*—Number of petals under normal conditions: 30–35.
- *Color.*—Center of flower: upper side of petals: near 44A. Reverse side of petals: near 46C and 46D. Base of petals: point of attachment nearly white. General tonality from a distance: red 44A.
- *Variegations.*—An occasional pink streak on outer petals.
- *Discoloration.*—General tonality at end of first day: none. Third day: none.
- *Fragrance.*—Slight.

Petals:
- *Texture.*—Thick.
- *Shape.*—Round.
- *Form.*—Tips slightly recurved.
- *Arrangement.*—Imbricated. Petaloids in center, few.
- *Persistence.*—Drop off cleanly.
- *Lastingness.*—On the plant, long. As cut flower, long.

Reproductive parts:
- *Anthers.*—Large, many. Color, Red (53B) with Yellow (23C) edges. Arrangement, regular around styles.
- *Filaments.*—Color: Red, 53B.
- *Pollen.*—Gold yellow.

*Styles.*—Color: Red 43C.
*Stigmas.*—Color: white to yellow.

PLANT

Form: Bush.
Growth: Very vigorous, upright. Reaching 7½′ at Irvine, Calif., the second year after planting, with normal pruning and cultural practices.
Foliage: Number of leaflets on normal mid-stem leaves: 5, sometimes 7.
*Size.*—Large.
*Quantity.*—Normal.
*Color.*—New foliage: near Greyed Red 178B. Old foliage: dark green, near 139A.
Leaflets:
*Shape.*—Oval pointed.
*Texture.*—Upper side, leathery.
*Edge.*—Serrated.
*Serration.*—Single, small.
*Petiole.*—Rachis: green and reddish color. Small prickles on upper edges; a few large prickles on green, lower side.

*Stipules.*—Long.
*Disease resistance.*—Normal resistance to mildew and blackspot under normal growing conditions at Irvine, Calif.
Wood:
*New wood.*—Color: reddish. Bark: smooth.
*Old wood.*—Color: green. Bark: smooth.
Prickles:
*Quantity.*—On main stalks from base, few. On laterals from stalk, few.
*Form.*—Narrow base, medium, hooked downward.
*Color when young.*—Brown.
*Position.*—Irregular.
Small Prickles:
*Quantity.*—None. On laterals, none.

I claim:

1. A new and distinct variety of rose plant of the hybrid tea class, substantially as herein shown and described, characterized particularly as to novelty by the unique combination of its vigorous tall bush, long stiff stems with few thorns, dark green, medium sized leaves, its uniform red flower color and light fragrance.

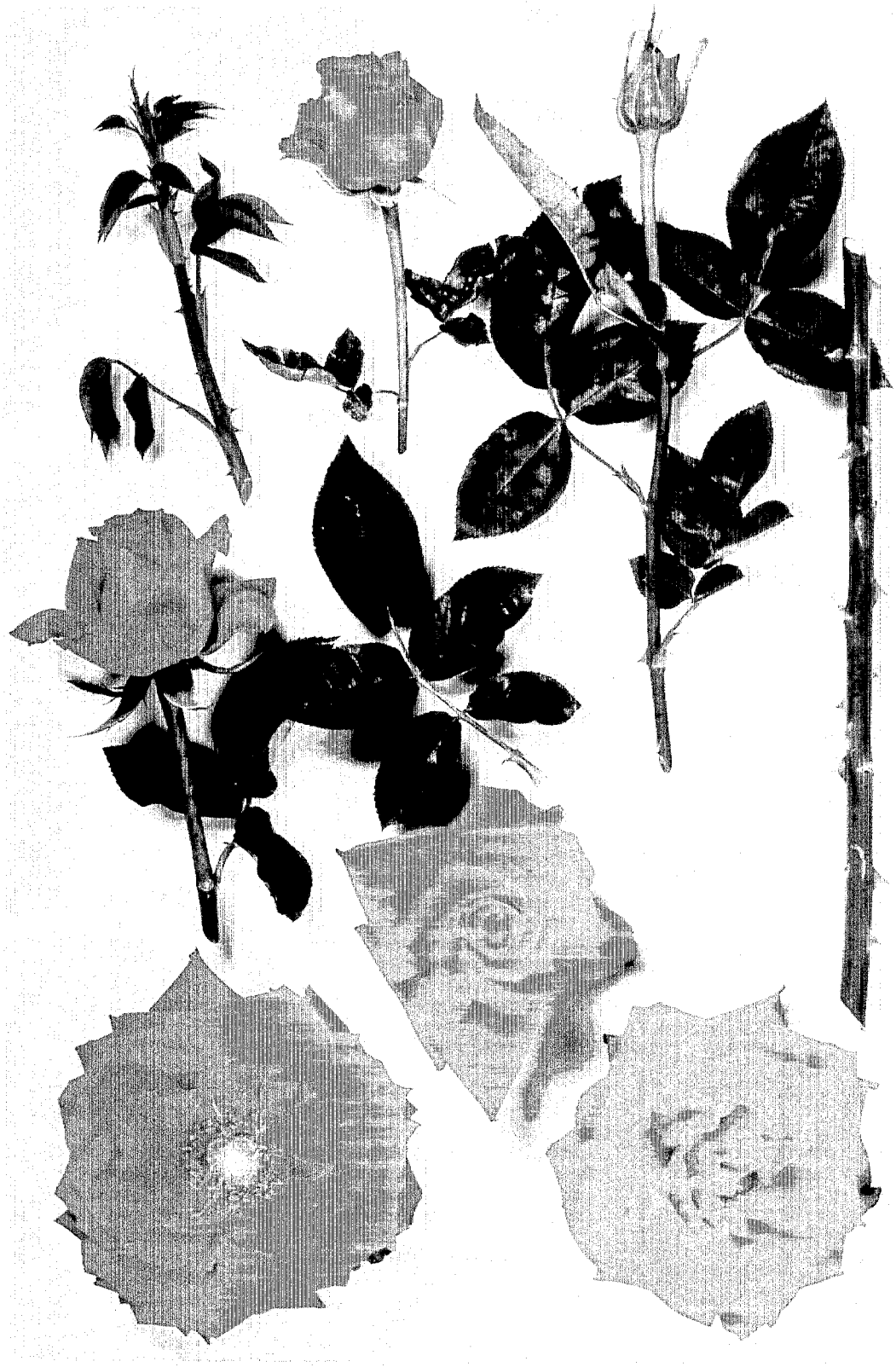

* * * * *